United States Patent
Fix et al.

(10) Patent No.: US 8,698,319 B2
(45) Date of Patent: Apr. 15, 2014

(54) ELECTRONIC COMPONENT

(75) Inventors: Richard Fix, Gerlingen (DE); Frederik Schrey, Leonberg (DE); Oliver Wolst, Singapore (SG); Ingo Daumiller, Dettingen (DE); Alexander Martin, Regensburg (DE); Martin Le-Huu, Korntal (DE); Mike Kunze, Pfaffenhofen (DE)

(73) Assignee: Robert Bosch GmbH, Stuttgart (DE)

( * ) Notice: Subject to any disclaimer, the term of this patent is extended or adjusted under 35 U.S.C. 154(b) by 217 days.

(21) Appl. No.: 12/998,680

(22) PCT Filed: Nov. 17, 2009

(86) PCT No.: PCT/EP2009/065296
§ 371 (c)(1),
(2), (4) Date: Jul. 25, 2011

(87) PCT Pub. No.: WO2010/057879
PCT Pub. Date: May 27, 2010

(65) Prior Publication Data
US 2011/0272747 A1      Nov. 10, 2011

(30) Foreign Application Priority Data

Nov. 20, 2008  (DE) .......................... 10 2008 043 929

(51) Int. Cl.
*H01L 23/528*      (2006.01)

(52) U.S. Cl.
USPC .... 257/775; 257/253; 257/773; 257/E23.017; 438/49

(58) Field of Classification Search
USPC ............... 257/253, 414, 768, 773, E23.017, 257/E29.242, 775; 438/49
See application file for complete search history.

(56) References Cited

U.S. PATENT DOCUMENTS

| | | | | |
|---|---|---|---|---|
| 4,016,524 A | * | 4/1977 | Pompei et al. | 338/34 |
| 4,903,115 A | * | 2/1990 | Barbu et al. | 257/587 |
| 4,922,311 A | * | 5/1990 | Lee et al. | 257/288 |
| 5,698,771 A | | 12/1997 | Shields et al. | |
| 6,031,291 A | * | 2/2000 | Sato et al. | 257/774 |
| RE36,938 E | * | 10/2000 | Chan et al. | 438/612 |
| 8,072,076 B2 | * | 12/2011 | Hsu et al. | 257/768 |
| 2004/0178468 A1 | | 9/2004 | McFarland et al. | |
| 2007/0126061 A1 | | 6/2007 | Dodabalapur et al. | |
| 2007/0132043 A1 | * | 6/2007 | Bradley et al. | 257/414 |
| 2009/0090170 A1 | | 4/2009 | Dass et al. | |
| 2011/0193140 A1 | * | 8/2011 | Fix et al. | 257/253 |
| 2011/0197657 A1 | * | 8/2011 | Gole | 73/31.05 |
| 2013/0075794 A1 | * | 3/2013 | Bradley et al. | 257/253 |

FOREIGN PATENT DOCUMENTS

| | | |
|---|---|---|
| DE | 10 2005 008 051 | 8/2006 |
| FR | 2 368 802 | 5/1978 |
| JP | 2003-232763 | 8/2003 |
| JP | 2006-317155 | 11/2006 |

OTHER PUBLICATIONS

A. Schütze et al.: "In-plane interdigitated (IPID) electrodes for thin film applications" Fresenius J. Anal. Chem., Bd. 346, 1993, pp. 380-382.

* cited by examiner

*Primary Examiner* — Allan R Wilson
(74) *Attorney, Agent, or Firm* — Kenyon & Kenyon LLP

(57) ABSTRACT

An electronic component includes a printed conductor structure on a substrate, as well as a film which contacts the printed conductor structure. The film has a smaller layer thickness than the printed conductor. The printed conductor structure has a region which is covered by the film for the purpose of contacting.

9 Claims, 1 Drawing Sheet

ELECTRONIC COMPONENT

BACKGROUND OF THE INVENTION

1. Field of the Invention

The present invention relates to an electronic component having a printed conductor structure on a substrate.

2. Description of Related Art

Electronic components generally include a printed conductor structure on a substrate. Such electronic components may also have a thin film which contacts the printed conductor structure. The film generally has a smaller layer thickness than the printed conductor structure. Such electronic components are used, for example, as semiconductor-based gas-sensitive field effect transistors in sensor system applications. The film, which has a smaller layer thickness than the printed conductor structure, usually represents the gate electrode. Action by a gas to be detected generally results in a change in the current flowing through the transistor from the source electrode to the drain electrode.

To allow gas detection with the aid of semiconductors, surfaces are necessary which are permeable at least to individual constituents of the gas species to be detected. These may be components of a gas mixture as well as constituents of a gas molecule. Thus, for detecting ammonia, for example, gas-sensitive field effect transistors are used which are permeable to hydrogen, for example. The permeability is generally ensured by thin and/or porous layers. The thickness of these layers is generally in a range of 1 nm to 100 nm. In addition, in particular, the design of the porous layer as an electrically conductive film is advantageous, since this porous layer may then be used, for example, as a gate electrode of the semiconductor component.

However, it has been shown that in particular at high operating temperatures and in corrosive environments such thin, gas-sensitive layers frequently break down due to degradation. It has been shown that the degradation occurs primarily at the bridging of steps or edges and at the connection to thicker films. However, such steps or edges are present on the semiconductor components due to the successive deposition of various materials, and usually have a height in the range of 10 nm to 1 μm. The connection of the thin layer to a thicker film is usually used for electrically contacting the porous layer.

A gas-sensitive field effect transistor for detecting hydrocarbons is described in U.S. Pat. No. 5,698,771, for example.

BRIEF SUMMARY OF THE INVENTION

An electronic component which is designed according to the present invention includes a printed conductor structure on a substrate, as well as a film which contacts the printed conductor structure. The film has a smaller layer thickness than the printed conductor structure. The printed conductor structure has a region which is covered by the film or is situated thereon for the purpose of contacting.

A larger contact surface is achieved as a result of the printed conductor structure having a region which is covered by the film or is situated thereon for the purpose of contacting. In addition, contacting is not just carried out on a vertical surface at which the two films abut one another.

Tearing off of the film having a smaller layer thickness from the printed conductor structure may be prevented in this way. Stabilization of the thin film and its electrical contacting is thus achieved. In the electronic components known from the related art, such tearing results, for example, due to the fact that different thermal expansions occur at high temperatures, which are necessary for gas sensors, for example, and which generally range from 25° C. to 800° C. In addition, with increasing operating temperature, for example, the selection of a suitable film material is more problematic. For example, platinum is increasingly mobile above temperatures of approximately 500° C., and has a tendency toward agglomeration and crystal formation. As a result, the surface covering becomes inhomogeneous.

Additional stresses occur due to temperature changes. Thin films in particular are distorted by materials situated underneath which have different coefficients of thermal expansion. This results in tearing off of the thin films primarily at steps. In this context, "steps" are understood to mean height differences greater than several nanometers. However, such non-planar transitions are unavoidable for many high-temperature semiconductor structures. Such edges result, for example, from mesa structuring, trenches, printed conductors, passivations, or insulation layers.

The risk of the thin films tearing off at steps or edges is increased due to the fact that necessary semiconductor processes do not allow isotropic deposition of the thin films. In addition, coordination of multiple processes with one another is not possible without a certain degree of imprecision. The imprecision results, for example, from the resolution of the lithography during manufacture. This prevents exact adjustment of multiple layers to one another.

However, by using the electronic component according to the present invention, in which the printed conductor structure has a region which is covered by the film for the purpose of contacting, such tearing off is avoided due to the fact that not just vertical regions are connected to one another; rather, horizontal regions are also connected via the covering. The contacting thus remains, even in the case of different thermal expansions of the materials of the various layers.

A common height of a printed conductor structure as used, for example, in gas-sensitive field effect transistors, is in a range of 10 nm to 1 μm. The thin film, which contacts the printed conductor structure and has a smaller layer thickness than the printed conductor structure, usually has a layer thickness in the range of 1 nm to 100 nm. The layer thickness of the film is generally 2 to 1000 times smaller than the layer thickness of the printed conductor structure.

To achieve stable contacting and to avoid tearing off due to different thermal expansions, for example, in another specific embodiment the region which is covered by the film has a smaller layer thickness than the film. The covered region preferably has a height in the range of 1 nm to 200 nm. As a result of the layer thickness of the covered region being smaller than that of the film which covers the region, the situation is avoided that a step which corresponds at least to the thickness of the film must be overcome when the film is applied. Thus, a continuous film which overcomes the step at the end of the covered region may be provided when it is applied. The risk of tearing due to different thermal expansions, for example, is thus avoided.

In one alternative specific embodiment, the region which is covered by the film adjoins a further layer, the covered region and the further layer having essentially the same layer thickness. The thin film usually also covers the further layer which adjoins the region that is covered by the film. The formation of a step which must be overcome by the film having a smaller layer thickness is avoided due to the essentially identical layer thickness of the covered region and the further layer. The film may have a flat design. Such a layer thickness which is essentially uniform may be provided, for example, by using a self-adjusting process which is known to those skilled in the art. Flat transitions, i.e., a uniform layer thickness, may be provided in particular when a self-adjusting process is used for producing the layers.

The material from which the further layer is made is a semiconductor material or insulation material, for example. The material from which the further layer is made is preferably a suitable gate insulator for field effect transistors. Suitable insulation materials are $SiO_2$, SiON, $Si_3N_4$, SiC, $Al_2O_3$, or SiAlON, for example.

The material from which the printed conductor structure is made preferably has good electrical conductivity, and may be applied in particular as a thin layer on the substrate, using suitable processes. The printed conductor structure is applied by electron beam evaporation or metal sputtering processes, for example. Alternatively, however, electrolytic or currentless deposition on the substrate is possible. However, in order to produce a sufficiently small layer thickness of the region which is covered by the film for the purpose of contacting, this region in particular is preferably produced by electron beam evaporation or metal sputtering processes. Suitable materials for the printed conductor structure are selected, for example, from the group composed of titanium, platinum, gold, aluminum, copper, chromium, nickel, and tantalum, and compounds and alloys of these elements.

The material of the film, which has a smaller layer thickness than the printed conductor structure, is also preferably selected from the group composed of titanium, platinum, gold, aluminum, copper, chromium, nickel, and tantalum, compounds of these elements with oxygen, nitrogen, carbon, and silicon, and alloys of these elements. The advantage of using these elements is that they have good electrical conductivity. In addition, the tendency toward oxide formation is low, or may be minimized by providing an oxide layer on the surface. The situation is thus avoided that the material of the printed conductor structure or of the film experiences a loss in conductivity due to oxidation, and as a result the functionality of the electronic component is reduced or even completely lost.

The electronic component is a gas-sensitive field effect transistor, for example. To allow use of the electronic component as a gas-sensitive field effect transistor, the thin film which covers the region at the printed conductor structure is used as a gate electrode, for example. The film is preferably porous. Permeability to individual constituents of a gas species to be detected is achieved due to the porosity. Besides a porous electrically conductive film, however, it is also possible that the thin film is electrically conductive and solid, and a porous structure is applied to the film. However, it is preferred that the film is porous. In particular for use as a gas-sensitive field effect transistor, it is further preferred that the porous film contains a catalytically active substance on which, for example, a gas to be detected is split into its elements in an accelerated manner.

DETAILED DESCRIPTION OF THE INVENTION

Figure 1:
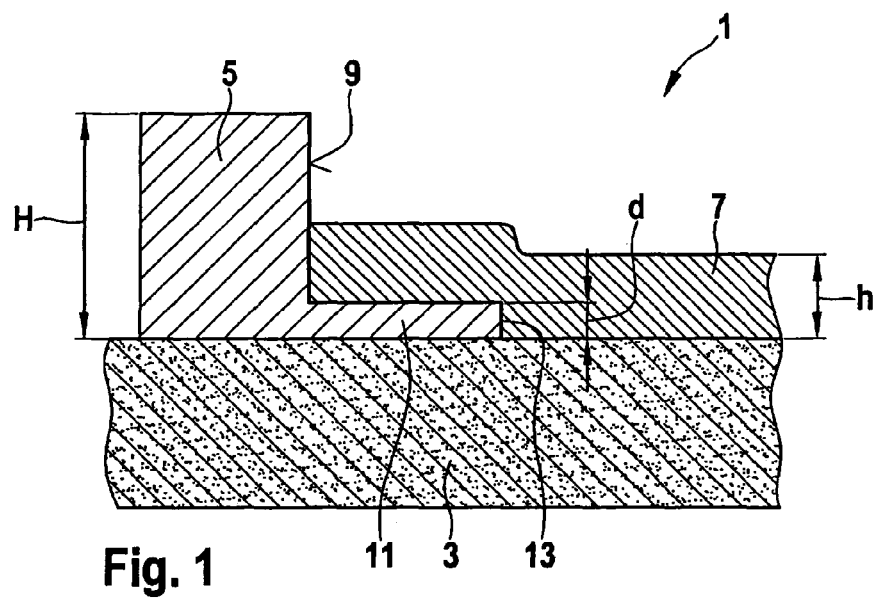
FIG. 1 shows a detail of an electronic component in a first specific embodiment.

FIG. 1 illustrates a cross section of a detail of an electronic component. An electronic component 1 includes a substrate 3 to which a printed conductor structure 5 is applied.

Substrate 3 may be made of any desired material known to those skilled in the art. Substrate 3 is usually made of an electrically insulating material or a semiconductor material, for example. The selection of the material for substrate 3 depends on the intended use of the electronic component. Electrically insulating materials of which substrate 3 may be made are sapphire or $SiO_2$, for example.

If the electronic component is to be used as a gas-sensitive field effect transistor, for example, substrate 3 is preferably made of a semiconductor material. Typically used semiconductor materials are, for example, semiconductor materials having a band gap greater than 2 eV. Of these, GaN and SiC are particularly preferred.

Printed conductor structure 5 is usually made of a material having good electrical conductivity. Suitable materials for printed conductor structure 5 are metals, for example. Suitable metals are preferably selected from the group composed of titanium, platinum, gold, aluminum, copper, chromium, nickel, and tantalum, and the compounds and alloys thereof. Printed conductor structure 5 may be applied using any desired method known to those skilled in the art. Thus, printed conductor structure 5 may be deposited on substrate 3 using currentless or electroplating processes. Further processes for producing printed conductor structure 5 are electron beam evaporation or metal sputtering processes, for example.

Electronic component 1 also includes a thin film 7. Thin film 7 has a layer thickness h which is smaller than height H of printed conductor structure 5.

In electronic components known from the related art, thin film 7 contacts printed conductor structure 5 at lateral surface 9 thereof. An electrical connection is thus ensured by only a narrow vertical contact surface. This surface results from the product of height h and the width of thin film 7. High temperatures at which the electronic component for example, may be used and/or mechanical strains may result in tearing off at the transition region. This results in an interruption of the electrical contacting. To avoid such tearing, in one electronic component 1 designed according to the present invention, printed conductor structure 5 includes a region 11 which is covered by thin film 7. Thus, in addition to vertical contacting at lateral surfaces 9 of printed conductor structure 5, a horizontal connection via the surface at which thin film 7 covers region 11 also results. The contact surface is thus enlarged by a factor of several times. In addition, contacting may also occur at lateral surface 9 of printed conductor structure 5.

As a result of the contacting at lateral surface 9, and in particular in covered region 11 of printed conductor structure 5, tearing off of thin film 7 from printed conductor structure 5 at different thermal expansions, for example, is avoided. The contacting of thin film 7 and printed conductor structure 5 is stabilized.

Thin film 7 may tear off in particular when thin film 7 is made of a different material than printed conductor structure 5. However, suitable materials for thin film 7 are generally the same as for printed conductor structure 5. Thus, for example, metals such as titanium, platinum, gold, aluminum, copper, chromium, nickel, and tantalum and compounds and alloys thereof are suitable. In particular for use in gas-sensitive electronic components, thin film 7 preferably contains a catalytically active material.

To allow covering of covered region 11 and to achieve a continuous film 7 in this region, layer thickness d of covered region 11 is preferably smaller than layer thickness h of thin film 7. Maximum layer thickness d of covered region 11 corresponds to layer thickness h of thin film 7. However, layer thickness d of covered region 11 is preferably smaller than layer thickness h of thin film 7. A continuous thin film 7 is obtained due to small layer thickness d of covered region 11. Tearing off does not occur in the region of terminating edge 13 of covered region 11.

Covered region 11 is produced using any desired, suitable method known to those skilled in the art. Covered region 11 of printed conductor structure 5 is preferably produced by electron beam evaporation or a metal sputtering process, since a targeted layer thickness d may be set, and correspondingly thin films may be produced, using these processes.

Depending on the production method for printed conductor structure 5, covered region 11 is applied after printed conductor structure 5 is produced or at the same time that printed conductor structure 5 is produced. In general, however, printed conductor structure 5 is produced first, and covered region 11 is subsequently produced in the regions in which thin film 7 is to contact printed conductor structure 5.

Depending on the planned use of electronic component 1, thin film 7 may be closed or porous. In particular when electronic component 1 is used as a gas-sensitive field effect transistor, as employed in gas sensors, for example, it is preferred that thin film 7 is porous. Thin film 7 is then used as a gate electrode of the field effect transistor.

Figure 2:
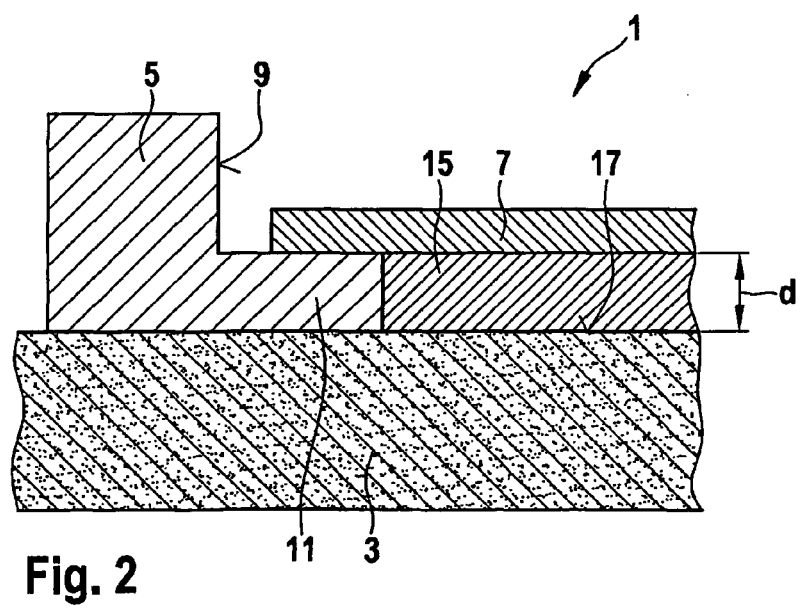
FIG. 2 shows a detail of an electronic component in a second specific embodiment.

One alternative specific embodiment of an electronic component designed according to the present invention is illustrated in FIG. 2.

The specific embodiment of electronic component 1 illustrated in FIG. 2 differs from that illustrated in FIG. 1 in that a further layer 15 is provided between substrate 3 and thin film 7. Further layer 15 adjoins covered region 11 of printed conductor structure 5. The layer thickness of further layer 15 corresponds to layer thickness d of covered region 11.

Further layer 15 may be produced using a self-adjusting process, for example. An edge-free transition is thus achieved in the region in which further layer 15 adjoins covered region 11.

For example, a self-adjusting process is carrying out various successive process steps, using a single lithographic mask. The aim, in principle, is to avoid adjustment imprecision of two lithographic masks with respect to one another. When further layer 15 does not adjoin printed conductor structure 5, which is generally the case in the related art, and which results, for example, from imprecision of multiple lithographic masks, this results in steps which must be overcome by the thin film. When a layer thickness of further layer 15 and of printed conductor structure 5 is greater than that of thin film 7, thin film 7 may tear off in the region of the steps. In addition, this results in contact only at lateral surface 9 of printed conductor structure 5, resulting in only a small contact region which in addition may tear due to different thermal expansions of the materials.

As a result of the design of covered region 11, which adjoins further layer 15 and has essentially the same layer thickness d as further layer 15, edges which must be overcome by thin film 7 are avoided.

For manufacture, covered region 11 is generally produced first. Printed conductor structure 5 is then deposited thereon. Due to its characteristics and function, this printed conductor structure has an edge height that is usually greater than 10 nm, in general greater than 100 nm. After the printed conductor structure is produced, full-surface deposition of further layer 15 is generally carried out. The further layer is then coated with the aid of photoresists, which are usually negative, in order to achieve negative edge profiles which are suitable for subsequent processes. The masking is usually carried out using suitable exposure processes such as contact copy or stepper exposure. After the photoresist mask is developed, the locations between further layer 15 and lateral surface 9 of printed conductor structure 5 are exposed from the photoresist. As an alternative to a lithographic process using a photoresist, however, a two- or multilayer photoresist process, for example, may also be selected. After the development, the lowermost photoresist layer undergoes greater expansion than the photoresist situated thereabove, resulting in a typical liftoff profile which simplifies the subsequent process steps. Thus, back-etching of further layer 15 subsequent to the development is carried out only at locations which are not covered by photoresist. The back-etching is usually carried out using a dry chemical etching process, but may also be achieved using suitable wet chemical methods. Such methods are known to those skilled in the art. Depending on the materials selected for substrate 3 and further layer 15, the etching process is terminated at boundary face 17 between further layer 15 and substrate 3. This etching process, which is referred to as back-etching, is then followed by full-surface metal plating using common, standard deposition processes without prior detachment of the photoresist mask, the layer thickness of the deposited metal layer being selected to be exactly the same as the layer thickness of further layer 15. The photoresist together with the metal deposited on the photoresist is removed in a subsequent liftoff process. Negative flanks, i.e., the liftoff profile of the photoresists, assist in this process. This results in an edge- and gap-free transition between the various layers 11 and 15.

Semiconductor materials or insulation materials, for example, are suitable as material for the further layer. GaN and SiC are examples of suitable semiconductor materials, and $SiO_2$ and $Si_3N_4$ are examples of suitable insulation materials.

Alternatively, an identical height of covered region 11 and further layer 15 may also be achieved by chemical-mechanical polishing, for example. The layer which is deposited first, generally further layer 15, must be suitable as a polishing material and must be structured. The second layer, generally covered region 11, is subsequently deposited in such a way that it overlaps the first layer. Planarization of the layers is achieved using a chemical-mechanical polishing process, known to those skilled in the art, which terminates at the height of the first layer, generally further layer 15. This results in a completely even transition for thin film 7.

An electronic component 1 produced in this manner is suitable, for example, as a semiconductor-based gas sensor, for example a gas sensor for gas species containing combustible gases, nitrogen oxides, or oxygen.

What is claimed is:

1. An electronic component, comprising:
   a substrate;
   a printed conductor structure positioned on the substrate and directly contacting at least a portion of the substrate; and
   a film positioned above the substrate and directly contacting the printed conductor structure;
   wherein a layer thickness of the film is smaller than a layer thickness of the printed conductor, and wherein the printed conductor structure has a selected region which is covered by at least a portion of the film and contacting the film, and
   wherein a layer thickness of the selected region of the printed conductor structure is smaller than a layer thickness of the portion of the film covering the selected region of the printed conductor structure.

2. The electronic component as recited in claim 1, wherein the selected region of the printed conductor structure covered by at least a portion of the film has a layer thickness in the range of 1 nm to 200 nm.

3. The electronic component as recited in claim 1, wherein the substrate is a semiconductor material.

4. The electronic component as recited in claim 3, wherein the material for the printed conductor structure includes at least one of titanium, platinum, gold, aluminum, copper, chromium, nickel, and tantalum.

5. The electronic component as recited in claim 3, wherein the material for the film includes at least one of titanium, platinum, gold, aluminum, copper, chromium, nickel, and tantalum.

6. The electronic component as recited in claim 5, wherein the film is porous.

7. The electronic component as recited in claim 6, wherein the electronic component is a gas-sensitive field effect transistor.

8. An electronic component, comprising:
a substrate;
a printed conductor structure positioned on the substrate and directly contacting at least a portion of the substrate; and
a film positioned above the substrate and directly contacting the printed conductor structure;
wherein a layer thickness of the film is smaller than a layer thickness of the printed conductor, and wherein the printed conductor structure has a selected region which is covered by at least a portion of the film and contacting the film, and
wherein the selected region of the printed conductor structure covered by at least a portion of the film laterally adjoins a further layer, and wherein the selected region of the printed conductor structure and the further layer have substantially the same layer thickness.

9. The electronic component as recited in claim 8, wherein the substrate and the further layer are made of the same material.

* * * * *

UNITED STATES PATENT AND TRADEMARK OFFICE
CERTIFICATE OF CORRECTION

PATENT NO. : 8,698,319 B2 Page 1 of 1
APPLICATION NO. : 12/998680
DATED : April 15, 2014
INVENTOR(S) : Fix et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 209 days.

Signed and Sealed this

Twenty-ninth Day of September, 2015

Michelle K. Lee
*Director of the United States Patent and Trademark Office*